United States Patent
Rieger et al.

(10) Patent No.: US 9,956,115 B2
(45) Date of Patent: May 1, 2018

(54) DEVICE FOR CUTTING AND ASPIRATING TISSUE

(71) Applicant: GEUDER AG, Heidelberg (DE)

(72) Inventors: Frank Rieger, Malsch (DE); Rene Draheim, Sandhausen (DE); Dieter Frauenfeld, Heidelberg (DE); Volker Geuder, Heidelberg (DE)

(73) Assignee: GEUDER AG, Heidelberg (DE)

( * ) Notice: Subject to any disclaimer, the term of this patent is extended or adjusted under 35 U.S.C. 154(b) by 174 days.

(21) Appl. No.: 14/759,350

(22) PCT Filed: Jan. 20, 2014

(86) PCT No.: PCT/DE2014/200007
§ 371 (c)(1),
(2) Date: Jul. 6, 2015

(87) PCT Pub. No.: WO2014/117774
PCT Pub. Date: Aug. 7, 2014

(65) Prior Publication Data
US 2015/0335485 A1 Nov. 26, 2015

(30) Foreign Application Priority Data

Feb. 4, 2013 (DE) .................. 10 2013 201 784

(51) Int. Cl.
*A61F 9/007* (2006.01)
(52) U.S. Cl.
CPC .................. *A61F 9/00763* (2013.01)
(58) Field of Classification Search
CPC ............. A61F 9/00736; A61F 9/00763; A61B 17/32002; A61B 2017/320028
See application file for complete search history.

(56) References Cited

U.S. PATENT DOCUMENTS

| 4,011,869 A | * | 3/1977 | Seiler, Jr. ............ A61F 9/00763 |
| | | | 604/22 |
| 4,111,207 A | | 9/1978 | Seiler, Jr. |

(Continued)

FOREIGN PATENT DOCUMENTS

| CH | 704384 A2 | 7/2012 |
| DE | 102010050337 A1 | 5/2012 |
| WO | WO 1994/009711 A1 | 5/1994 |

OTHER PUBLICATIONS

The International Bureau of WIPO, International Preliminary Report on Patentability (English Translation of ISA's Written Opinion) for International Application No. PCT/DE2014/200007, dated Aug. 4, 2015, 7 pages, Switzerland.

(Continued)

*Primary Examiner* — Julie A Szpira
(74) *Attorney, Agent, or Firm* — Alston & Bird LLP (57) ABSTRACT

The present invention relates to a device for cutting and aspirating tissue from the human or animal body, in particular for use in vitrectomy, epiretinal membrane peeling, etc., with an outer tube (1), and with an inner tube (2) which is movable to and fro and concentrically in the outer tube (1) with slight play, wherein the outer tube (1) is closed at the free end and has, near the free end, at least one lateral opening (3) with at least one inner cutting edge (5), wherein the inner tube (2) is open at the free end and there has an outer cutting edge (4), and wherein the cutting edges cooperate in a cutting action during the movement of the inner tube (2) relative to the outer tube (1), advantageously characterized by a shaping measure in or on the outer tube (1) and/or in or on the inner tube (2), whereby the inner tube (2), at least in the area of the lateral opening (3), runs in the outer tube (1) with at least slight pretensioning.

18 Claims, 7 Drawing Sheets

(56) References Cited

U.S. PATENT DOCUMENTS

| | | | | |
|---|---|---|---|---|
| 4,513,745 | A * | 4/1985 | Amoils | A61F 9/00763 604/22 |
| 4,696,298 | A | 9/1987 | Higgins et al. | |
| 5,106,364 | A * | 4/1992 | Hayafuji | A61B 17/32002 30/208 |
| 5,458,112 | A * | 10/1995 | Weaver | A61B 10/0275 600/566 |
| 5,474,532 | A * | 12/1995 | Steppe | A61F 9/00763 604/22 |
| 5,630,827 | A * | 5/1997 | Vijfvinkel | A61B 10/0266 604/22 |
| 5,843,111 | A * | 12/1998 | Vijfvinkel | A61B 10/0266 604/22 |
| 5,911,701 | A * | 6/1999 | Miller | A61B 17/32002 604/22 |
| 6,258,111 | B1 * | 7/2001 | Ross | A61B 17/32002 606/171 |
| 6,695,821 | B1 * | 2/2004 | Sjaarda | A61M 3/0279 604/264 |
| 7,744,583 | B2 * | 6/2010 | Seifert | A61B 17/00491 604/507 |
| 8,313,501 | B2 | 11/2012 | Miller et al. | |
| 8,852,113 | B2 * | 10/2014 | Nishina | A61B 8/12 600/466 |
| 2013/0211439 | A1 | 8/2013 | Geuder | |
| 2014/0171997 | A1 * | 6/2014 | Nissan | A61F 9/00763 606/171 |

OTHER PUBLICATIONS

International Searching Authority (ISA), International Search Report for International Application No. PCT/DE2014/200007, dated May 22, 2014, 7 pages, European Patent Office, The Netherlands.

International Searching Authority, Written Opinion for International Application No. PCT/DE2014/200007, dated May 22, 2014, 5 pages, European Patent Office, Germany.

Geuder AG, Applicant's Response to the ISA's May 22, 2014 Written Opinion for International Application No. PCT/DE2014/200007, dated Jan. 13, 2015, 9 pages, Ullrich & Naumann, Germany.

* cited by examiner

DEVICE FOR CUTTING AND ASPIRATING TISSUE

CROSS REFERENCE TO RELATED APPLICATIONS

This application is a national stage application, filed under 35 U.S.C. § 371, of International Application No. PCT/DE2014/200007, filed Jan. 20, 2014, which claims priority to German Application No. 10 2013 201 784.7, filed Feb. 4, 2013, the contents of which as are hereby incorporated by reference in their entirety.

BACKGROUND

Technical Field

The invention relates to an apparatus for cutting and aspirating tissue from the human or animal body, in particular for use in vitrectomies, for retinal peeling, etc., having an outer tube, and an inner tube which is arranged concentrically inside the outer tube, with little play, in a manner allowing sliding back and forth, wherein the outer tube is closed on the free end thereof, and has at least one lateral opening, the same with at least one inner cutting edge, close to the free end, wherein the inner tube is open on the free end thereof, and has an outer cutting edge there, and wherein the cutting edges work together by cutting when the inner tube slides with respect to the outer tube.

This is, basically, a surgical cutting instrument for the purpose of removing tissue. It is possible to cut the tissue—on and/or in the body—with the instrument, and aspirate the same from and/or out of the body. Specifically, the instrument can be a very specific cutting instrument which can be used during a vitrectomy to destroy and/or break up the vitreous humor in the eye and remove/aspirate the same from the eye. In addition, it is possible by means of this instrument to remove blood, clotted blood, connective tissue alterations, as well as portions of the retina, during a retinal peeling. A device in this class is fundamentally suitable for use in eye surgery.

Description of Related Art

DE 10 2010 050 337 A1 is hereby named as part of the prior art, by way of example. A device in the class is known from this document, wherein both the outer tube and the inner tube thereof each have two lateral recesses with a dual cutting function. Similar devices are known from U.S. Pat. No. 5,474,532 and U.S. Pat. No. 5,106,364.

It is typical in the devices which define the class that the device must be implemented with extremely little play between the inner wall of the outer tube and the outer wall of the inner tube, such that the cutting edges work together in an ideal manner. The tissue should be cut by the cooperation of the cutting edges, and not, for example, squeezed or sheared. Devices strive to achieve an ideal cooperation of the cutting edges with the least possible play.

The device in question, particularly for use in eye surgery, must comprise the smallest possible dimensions. As such, there are devices in the class wherein the inner tube thereof has a wall thickness of four hundredths of a millimeter. The outer tube has an outer diameter in the range from 0.5 to 0.9 mm, and an inner diameter of 0.35 to 0.37 mm. Accordingly, the outer diameter of the inner tube must be matched to the inner diameter of the outer tube with the least possible play. This makes the construction thereof complicated, and therefore results in considerable manufacturing costs—specifically when the intention is to achieve sufficiently good cutting results.

BRIEF SUMMARY

The problem addressed by the present invention is that of implementing and advancing the device in the class in such a manner that a sufficiently good cutting result is achieved even with higher tolerance, wherein the device should have a simple construction and be cost-effective to produce.

The problem as stated above is addressed by the features of claim 1. According to the same, the device which defines the class is characterized by a measure which shapes the outer tube, in or on the same, and/or the inner tube, in or on the same, whereby the inner tube runs in the outer tube with at least a small amount of pretensioning, at least in the region of the lateral opening of the outer tube.

The invention is based on the idea that the inner tube running in the outer tube is pretensioned with respect to the inner wall of the outer tube—similar to the configuration of the blades of a pair of scissors. Such a pretensioning has the enormous advantage of making it possible to achieve a good cutting result even at high tolerances between the outer diameter of the inner tube and the inner diameter of the outer tube, specifically when the pretensioning is implemented at least in the region of the cutting edges which work together. It must be ensured that, by way of example, the front cutting edge of the inner tube does not catch in the lateral recess of the outer tube. Rather, the cutting edges must slide past each other, while cutting, and under the at least small amount of pretensioning. As a result of the bowed contour of the cutting edges, there is, in fact, a cutting movement and not, for example, a squeezing or shearing of the tissue.

The shaping measure provided according to the invention can be realized by different configurations. On the one hand, it is possible to press the inner tube against the inner wall of the outer tube at the point where the inner cutting edge of the outer tube is constructed. This can be realized by a deformation in the inner wall of the outer tube and/or the outer wall of the inner tube—to the greatest extent possible on the side which is opposite the opening of the outer tube. It can likewise be contemplated that the outer tube and/or the inner tube is angled with respect to the longitudinal axis, in such a manner that the inner tube runs in the outer tube under a pretensioning, and the cutting edges glide along each other and past each other in the process under pretensioning, as in the configuration of a pair of scissors. The following presents details of the concrete embodiments of the device according to the invention:

In the simplest case, the outer tube has a single lateral opening, such that the cutting edge in this case is a so-called single blade. The inner tube can have a single cutting edge on the free end thereof—that is, on the frontal opening. It can likewise be considered that, as part of such a configuration, the inner tube is also equipped with a lateral opening, wherein the opening of the inner tube has an outer cutting edge, in the region of the opening, which cuts during the backward movement. In such an embodiment, the device can cut during the forward and the backward movements, particularly due to the two cutting edges of the inner tube.

It can also be contemplated that the outer tube has a second lateral opening, near to the first lateral opening and/or shortly behind the same, with one or two inner cutting edges. As a result of this measure, it is possible to very significantly increase the cutting power, particularly if the inner tube also has a lateral opening, near to the free, open end, with one or two outer cutting edges, as has already been explained above. Each opening in this case can have a dual cutting function—for the forward movement and the backward movement.

A strut, which is small and/or thin, is advantageously constructed between the open end and the lateral opening of the inner tube, specifically for the purpose of having as little overlap in the cut as possible. A so-called suction shadow, which results in a pulse in the extraction rate, can essentially be entirely eliminated as a result. It is possible to achieve a maximum and consistent aspiration power/flow in the aspiration using this measure.

To facilitate the flow/aspiration power, the lateral opening of the inner tube has at least the same flow cross-section as the open end of the inner tube, thereby also helping to prevent the suction shadow as well. It is also advantageous if the openings of the inner tube each have approximately the same flow cross-section as the openings in the outer tube. It is also further advantageous if each position of the inner tube has the same effective flow cross-section with respect to the outer tube, for the purpose of specifically preventing a pulsing underpressure and therefore a pulsing aspiration power.

As explained above, a shaping measure is implemented according to the invention whereby there is at least a small pretensioning between the inner tube and the outer tube, so that the cutting edges work together particularly in the manner of a pair of scissors, thereby improving the cutting results.

Such a measure can be implemented by the inner wall of the outer tube being elevated inward at approximately the position opposite the lateral opening of the outer tube, such that something like a guide region is created on the inner wall of the outer tube. This guide region is either directly opposite the opening of the outer tube, or is arranged in front of, and likewise opposite, the same. The inner tube runs on the guide region, wherein the cutting edges are thereby pressed against each other at least slightly when passing each other. The elevated guide region included on the inner wall of the outer tube can be constructed as a deformation of the wall of the outer tube, for example as an indentation, a fluting, or a dimple, or also an addition of material to the inside of the wall, for example in the form of a welding spot or the like. As a result of these measures, it is possible to compensate for significant tolerances, wherein it is recognized according to the invention that it is not necessary for achieving a good cutting result that the inner tube is necessarily guided in the outer tube over the entire length thereof with the least possible tolerance. Rather, the teaching according to the invention turns away from the existing focus on the least possible play between the inner wall of the outer tube and the outer wall of the inner tube.

The previous explanations relate to the shaping measures performed on and/or in the wall of the outer tube. It can likewise be contemplated that, as a shaping measure, the outer wall of the inner tube, preferably in a region opposite the lateral opening of the outer tube, is curved outward such that the guide region is functionally assigned to the outer wall of the inner tube. The same details as those given for the measures named above, performed on and/or in the wall of the outer tube, apply here as well.

As explained above, the guide region can be implemented, in the outer tube, as a deformation directed from the outside inward, or in the inner tube as a deformation directed from the inside outward, or by a corresponding addition of material either to the inner wall of the outer tube or to the outer wall of the inner tube. A combination of these measures—with an offset to each other, and both on the outer tube and on the inner tube—can also be contemplated.

As an alternative or as a complement thereto, the at least small pretensioning between the inner tube and the outer tube can be implemented, at least in the region of the cutting edges, by the shaping measure being to bend the inner tube and/or the outer tube, before the opening and/or the openings, and therefore before the cutting edges, and/or to bend the same toward the longitudinal axis, in such a manner that the cutting edges pass by each other under at least a small amount of pretensioning when the inner tube glides back and forth in the outer tube. As a result of the bending—for example of the inner tube—it is possible to install the inner tube in the outer tube in such a manner that the cutting edge of the inner tube is pressed at least slightly against the inner wall of the outer tube, such that the cutting edges glide along each other when they pass the opening in the outer tube, under at least a small amount of pretensioning, and cut in an ideal manner similarly to the cutting edges of scissor blades.

To prevent tilting and jamming, and/or to facilitate fluid movement of the inner tube inside the outer tube, it can be contemplated and is additionally advantageous if the inner tube has two bendings oriented in different directions, particularly one bending as the fundamental generator of the pretensioning, on the one hand, and on the other hand an opposing bending as close as possible to the distal region, such that the angle of engagement of the cutting edges of the inner tube in the openings of the outer tube does not hinder the movement, and rather the outer wall of the inner tube and the inner wall of the outer tube are oriented at least nearly parallel to each other, at least in the frontal region, but also under pretensioning due to the first bending.

Specifically, the bending which is remote from the free end can be 1° to 2°, and the bending close to the free end can be 2° to 5°. If the device according to the invention is given the typical dimensions for use in ophthalmology, the bending which is remote from the free end is approximately 1 mm to 2 mm before the free end—for example 1.6 mm from the free end. The bending close to the free end is preferably constructed in the region of the lateral opening of the inner tube, preferably 0.1 mm to 0.5 mm before the free end, and particularly about 0.3 mm before the free open end of the inner tube. The two bendings can be constructed according to the explanations above in such a manner that the outer wall of the inner tube runs essentially parallel to the outer wall of the inner tube before the first bending, but slightly offset, specifically to generate the pretensioning of the inner tube against the outer tube, and particularly in the region of the opening of the outer tube, such that the cutting edges then work together effectively.

BRIEF DESCRIPTION OF THE FIGURES

At this point, there are various options for designing and implementing the teaching of the present invention in an advantageous manner. For this purpose, reference is hereby made on the one hand to the claims dependent on claim 1, and on the other hand to the following explanation of preferred embodiments of the invention with reference to the drawings. In the context of the explanation of the preferred embodiments of the invention and of the drawings, other generally preferred embodiments and implementations of the teaching are explained as well. In the drawings:

DETAILED DESCRIPTION OF VARIOUS EMBODIMENTS

Figure 1:
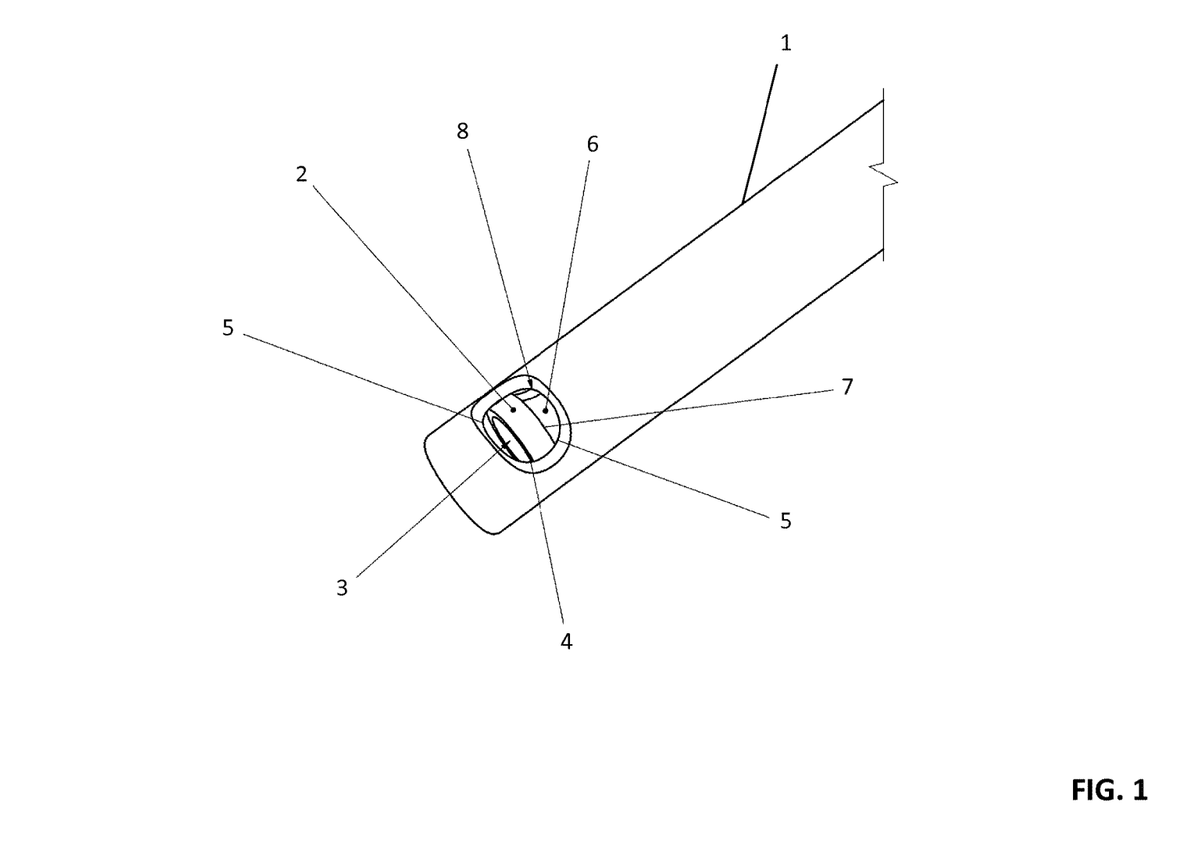
FIG. 1 shows a schematic view of one embodiment of a device according to the invention for the purpose of cutting and aspirating tissue from the human body, wherein the device is specifically a device for use in vitrectomies.

FIG. 1 shows a schematic partial view of a device according to the invention for cutting and aspirating tissue from the eye—particularly to use in vitrectomies.

The device comprises an outer tube 1 and an inner tube 2 which runs in the outer tube 1. The inner tube 2 is able to glide back and forth in the outer tube 1. FIG. 1 also shows that the outer tube 1 is closed on the distal end thereof. The inner tube 2, in contrast, has an opening 3 on the distal end thereof, which is equipped with an outer cutting edge 4. This outer cutting edge 4 works together with an inner cutting edge 5 of the outer tube 1, particularly when the inner tube 2 slides relative to the outer tube 1.

FIG. 1 likewise shows that the inner tube 2 is equipped with a lateral opening 6 which has an outer cutting edge 7 which cuts during the backward movement. Both outer cutting edges 4, 7 of the inner tube 2 work together with the inner cutting edge 5 of the lateral opening 8 of the outer tube 1.

Figure 2:
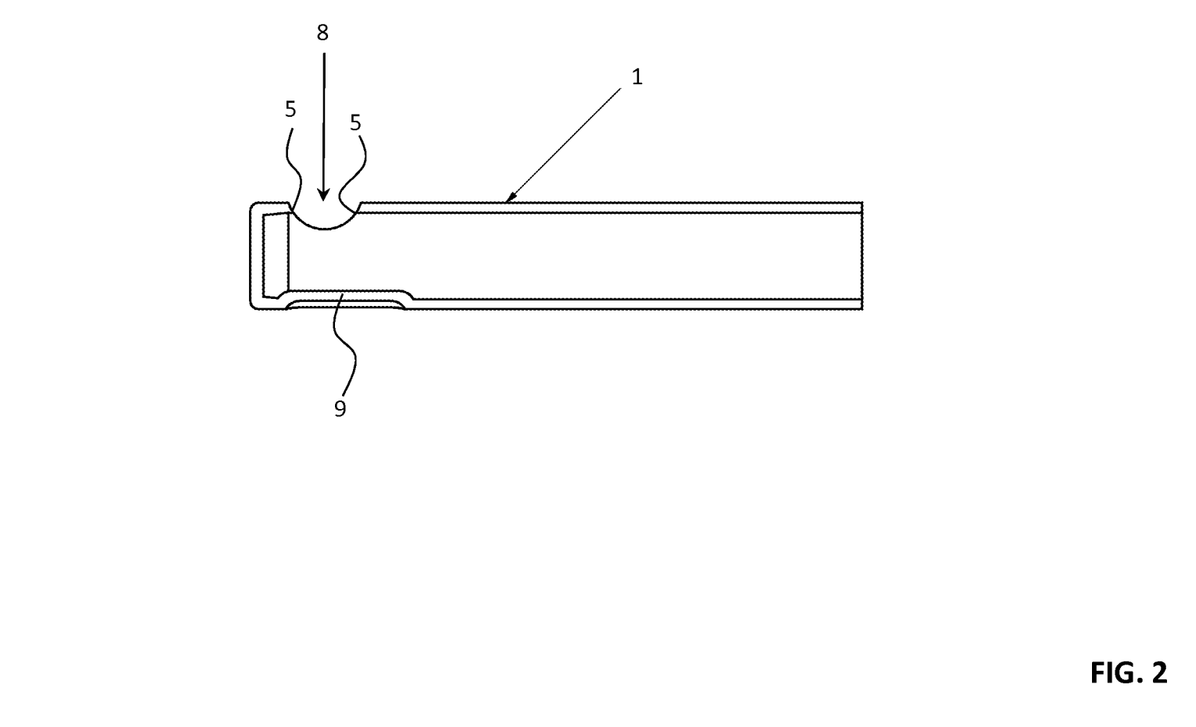
FIG. 2 shows a schematic cutaway side view of the outer tube of the subject matter in FIG. 1, as a part of a first variant.

FIG. 2 shows a schematic cutaway side view of an embodiment of the outer tube 1 shown in principle form, wherein the same is given a deformation on the side thereof opposite the lateral opening 8, specifically for the purpose of pressing the inner tube 2, which is not shown in FIG. 2, and its cutting edge 4, against the inner cutting edge 5 of the outer tube 1. As a result of this measure, it is possible to achieve the pretensioning according to the invention.

Figure 3:
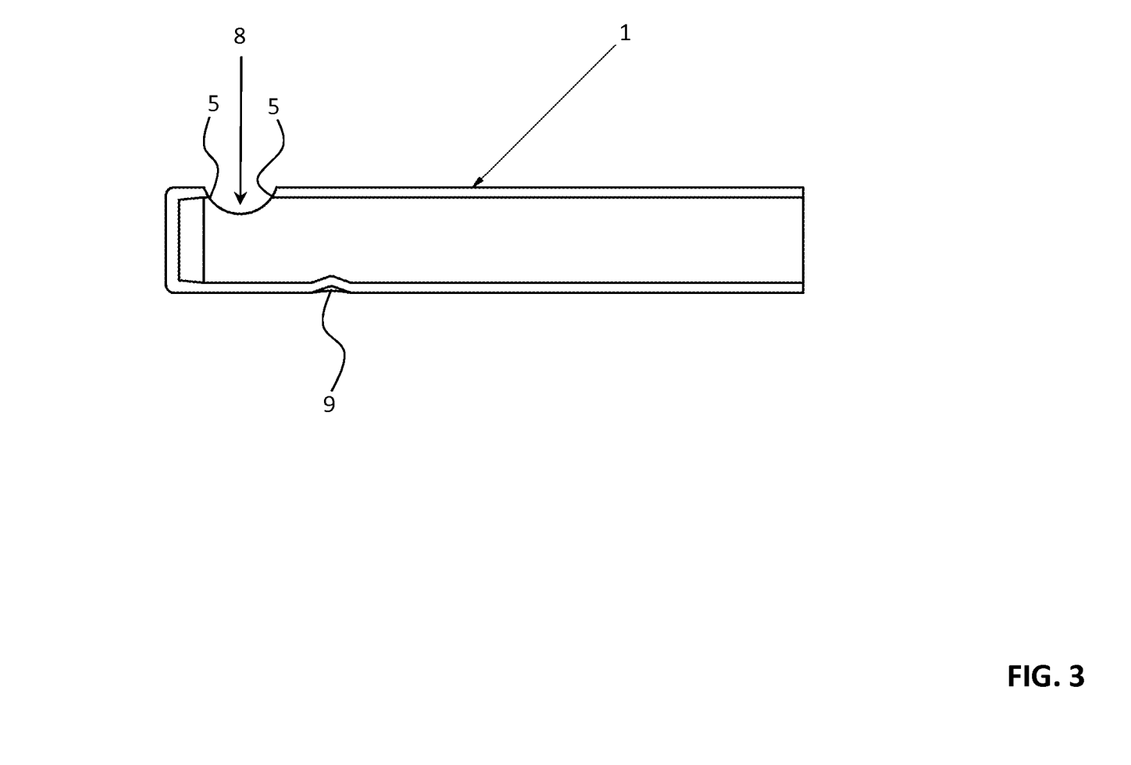
FIG. 3 shows a schematic cutaway side view of the outer tube of the subject matter in FIG. 1, as a part of a second variant.

FIG. 3 shows a further variant of the teaching according to the invention, realized by a measure on and/or in the outer tube 1, similar to the illustration in FIG. 2. Specifically, a seam and/or embossment 9 or the like is incorporated into the wall of the outer tube 1 such that the inner tube 2 likewise works, as a result of this measure, with its outer cutting edge 4 and/or its cutting edges 4, 7 pressed against the inner cutting edge 5 of the outer tube 1, particularly to improve the cutting result even if there is considerable play between the inner wall of the outer tube 1 and the outer wall of the inner tube 2.

Figure 4:
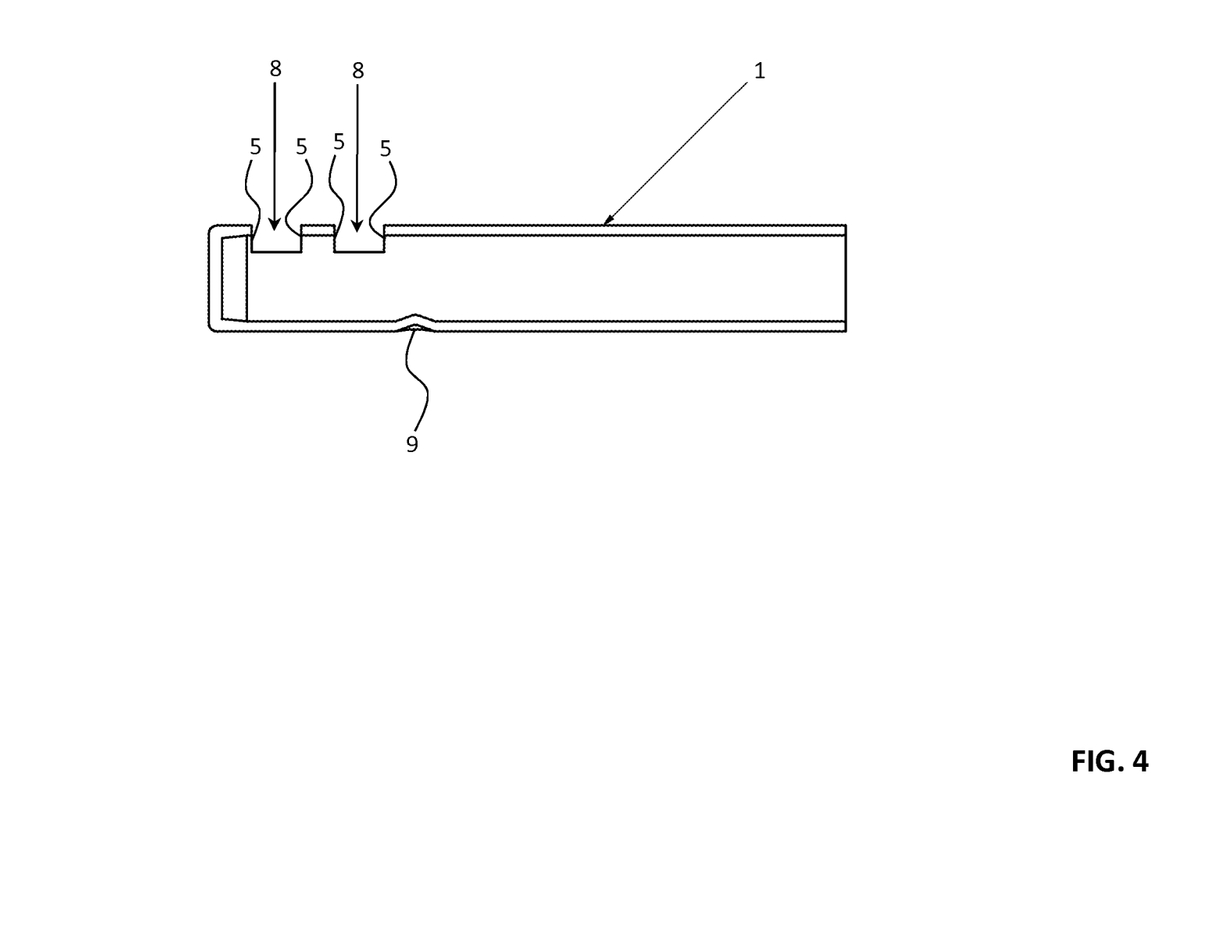
FIG. 4 shows a schematic cutaway side view of the outer tube of the subject matter in FIG. 1, as a part of a third variant.

According to FIG. 4, the outer tube 1 is equipped with two lateral openings 8. Accordingly, the configuration includes multiple cutting edges 5—with a maximum of four cutting edges 5 in the embodiment shown in FIG. 4—two for the forward movement and two for the backward movement. An embossment 9 creates the pretensioning when the inner tube 2 is inserted—as is shown in FIG. 1.

Figure 5:
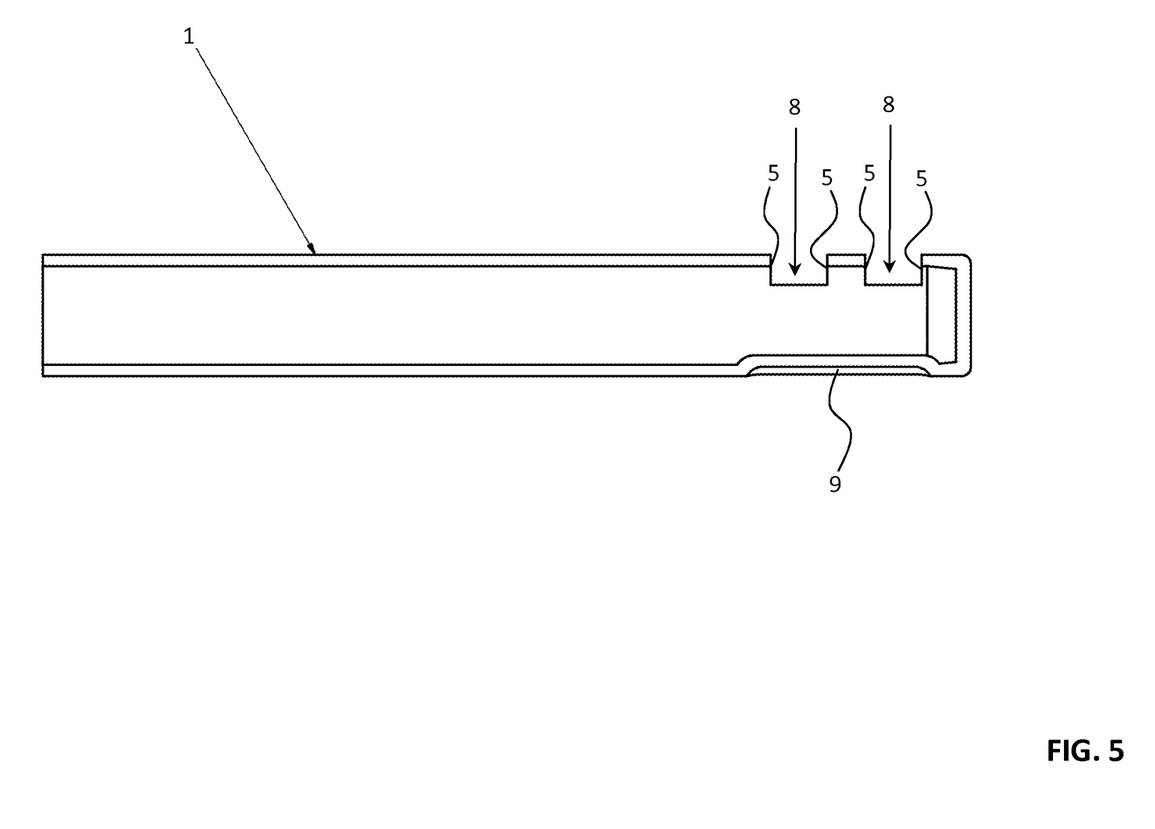
FIG. 5 shows a schematic cutaway side view of the outer tube of the subject matter in FIG. 1, as a part of a fourth variant.

The illustration in FIG. 5 is mirror-inverted with respect to the illustrations in FIGS. 2 to 4, wherein, compared to the illustration in FIG. 4, a flat embossment 9 is included, particularly to ensure the pretensioning over the entire distance of the two openings 8.

Figure 6:
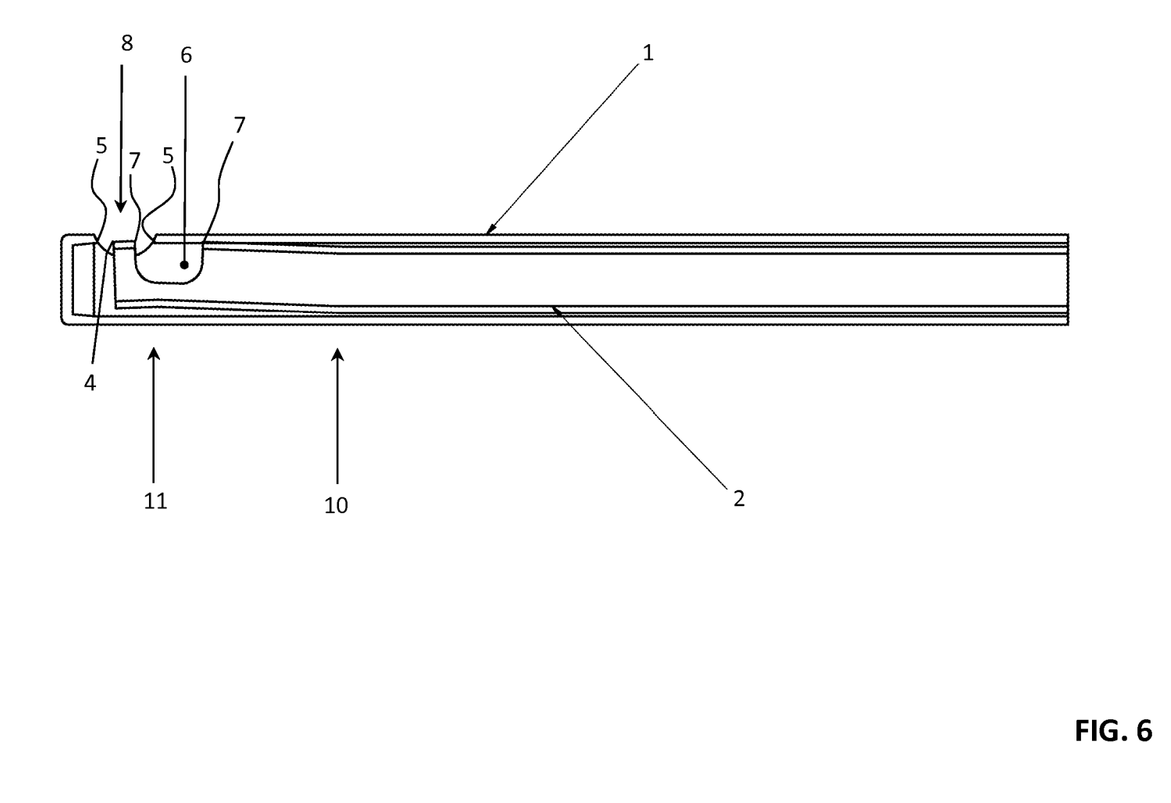
FIG. 6 shows a schematic cutaway side view of a further embodiment of the device according to the invention, wherein a pretensioning is generated between the inner tube and the outer tube by a doubly bent inner tube.

FIG. 6 shows a further measure for the purpose of implementing the pretensioning according to the invention between the outer tube 1 and the inner tube 2 running therein. The pretensioning is—as an alternative or a complement to the measures in FIGS. 2 to 5—realized by a double bending of the inner tube 2 with respect to the longitudinal axis, wherein the two bendings are seen in the single illustration of the inner tube 2 according to FIG. 7.

Figure 7:
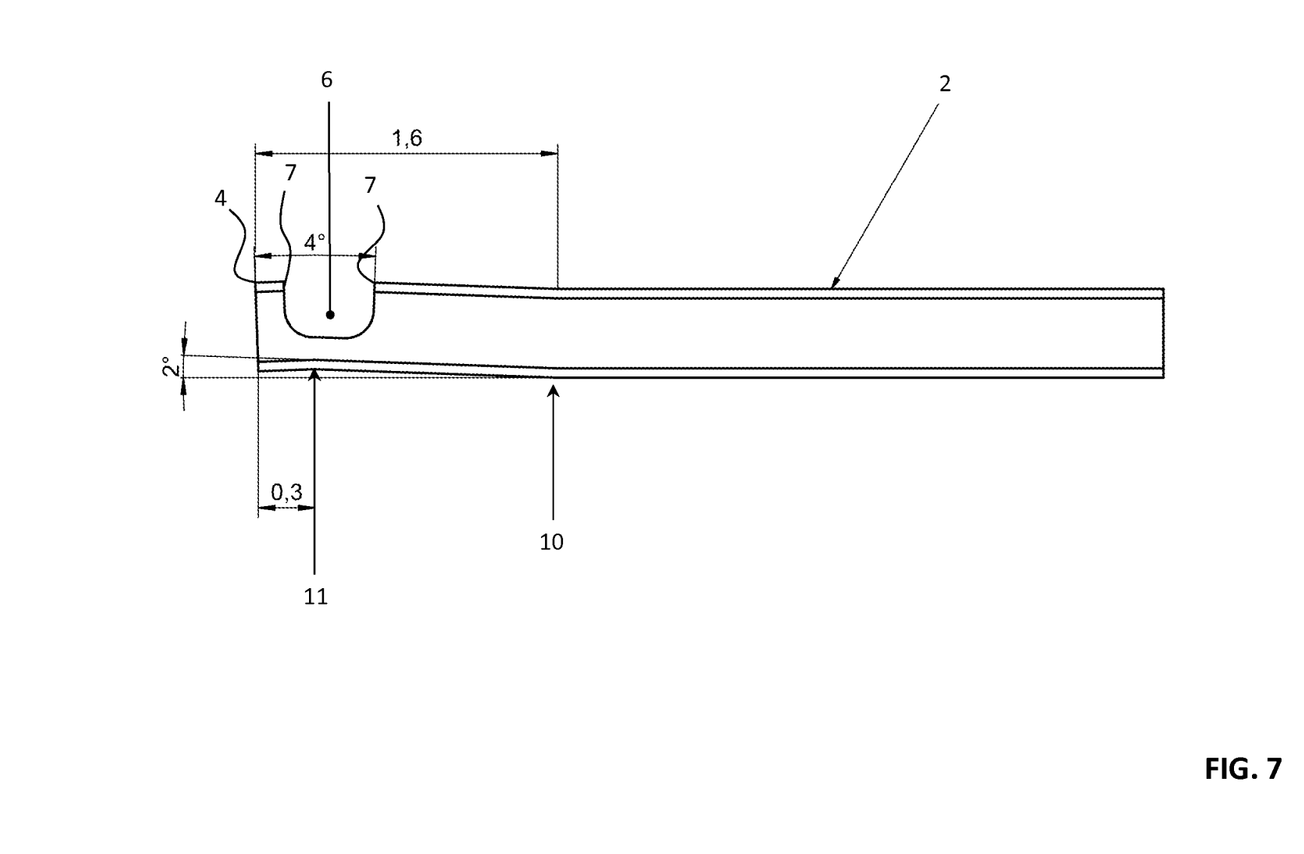
FIG. 7 shows a schematic cutaway side view of the doubly bent inner tube of the subject matter in FIG. 6.

In the embodiments shown in FIGS. 6 and 7, there is a first bending 10 at 1.6 mm before the distal end of the inner tube 2, particularly to press the outer cutting edges 4, 7 against the inner wall and/or the inner cutting edge 5 of the outer tube 1. For the purpose of, so to speak, "disarming", a second bending 11 is included which curves the inner tube 2 back, at least into a flush alignment, so that the outer wall runs approximately parallel to the outer wall before the first bending 10, specifically to prevent the outer cutting edges 4, 7 from engaging too strongly at the region of the lateral opening 8 of the outer tube 1. The second bending 11 facing the distal end is approximately 0.3 mm from the distal end in the embodiments shown in FIGS. 6 and 7, and is included in the region of the lateral opening 6 of the inner tube 2.

As regards further advantageous embodiments of the device according to the invention, reference is hereby made for the purpose of avoiding repetition to the general portion of the description and to the attached claims.

Finally, explicit reference is made to the fact that the exemplary embodiments of the device according to the invention described above are used only for explanation of the claimed teaching, but the teaching is not restricted to the exemplary embodiments.

LIST OF REFERENCE NUMBERS 1 outer tube
2 inner tube
3 opening at the distal end of the inner tube
4 outer cutting edge of the inner tube
5 inner cutting edge of the outer tube
6 lateral opening of the inner tube
7 outer cutting edge of the inner tube
8 lateral opening of the outer tube
9 embossment
10 first bending
11 second bending

The invention claimed is:

1. A device for cutting and aspirating tissue from the human or animal body, said device having a longitudinal axis and comprising:
   an outer tube (1); and
   an inner tube (2) arranged concentrically inside the outer tube (1), with little play, in a manner allowing sliding back and forth,
   wherein:
      the outer tube (1) is closed on the free end thereof, and has at least one lateral opening (8), the same having at least one inner cutting edge (5) close to the free end,
      the inner tube (2) is open on the free end thereof, and has an outer cutting edge (4),
      the cutting edges (4, 5) work together by cutting when the inner tube (2) slides with respect to the outer tube (1), with a shaping measure performed at least one of in or on the inner tube (2), the inner tube (2) runs in the outer tube (1) with at least a small amount of pre-tensioning, at least in the region of the lateral opening (3), the inner tube (2) is at least one of bent or is given a bending with respect to the longitudinal axis in such a manner that the cutting edges pass by each other under at least a small amount of pre-tensioning when the inner tube (2) glides back and forth in the outer tube (1), and the inner tube (2) has two bendings (10, 11) each oriented in a different direction, such that an outer wall of the inner tube (2) and an inner wall of the outer tube (1) are oriented at least nearly parallel relative to one other and the longitudinal axis, at least in a frontal region of the device adjacent the free ends of the inner and outer tubes (1, 2).

2. A device according to claim 1, wherein a measure performed on the outer tube (1), whereby the inner tube (2) runs in the outer tube (1) with at least a small amount of pre-tensioning, at least in the region of the lateral opening (3).

3. A device according to claim 1, wherein the outer tube (1) has a second lateral opening (8), near to the first lateral opening (8), with one or two inner cutting edges (5).

4. A device according to claim 1, wherein:

the lateral opening (6) of the inner tube (2) is positioned near to the free, open end of the inner tube (2), and the lateral opening (6) is provided with one or two outer cutting edges (4, 7).

5. A device according to claim 4, wherein a strut which is small/thin is constructed between the open end and the lateral opening (6) of the inner tube (2).

6. A device according to claim 4, wherein the lateral opening (6) of the inner tube (2) has at least the same flow cross-section as the open end of the inner tube (2).

7. A device according to claim 4, wherein the lateral opening (6) of the inner tube (2) has at least the same flow cross-section as the at least one lateral opening (8) in the outer tube (1).

8. A device according to claim 1, wherein, as the shaping measure, the inner wall of the outer tube (1) is elevated inward, approximately opposite the lateral opening (8), thereby producing a guide region.

9. A device according to claim 1, wherein, as the shaping measure, the outer wall of the inner tube (2) is elevated outward, preferably in a region opposite the lateral opening (6), thereby producing a guide region.

10. A device according to claim 8, wherein the guide region results from, in the case of the outer tube (1), a deformation oriented inward from the outside, and/or, in the case of the inner tube (2), from a deformation oriented outward from the inside.

11. A device according to claim 8, wherein the guide region is constructed as, in the case of the outer tube (1), an addition of material to the inside thereof, and/or, in the case of the inner tube (2), as an addition of material to the outside thereof.

12. A device according to claim 1, wherein, as the shaping measure, the outer tube (1) is bent and/or given a bending with respect to the longitudinal axis, before the opening (8), in such a manner that the cutting edges pass by each other under at least a small amount of pre-tensioning when the inner tube (2) slides back and forth in the outer tube (1).

13. A device according to claim 1, wherein the bending (10) which is remote from the free end is 1° to 2°, and the bending (11) closer than the bending (10) to the free end is 2° to 5°.

14. A device according to claim 1, wherein the bending (10) which is remote from the free end is 1 mm to 2 mm before the free end, and the bending (11) closer than the bending (10) to the free end is in the region of the lateral opening (6) of the inner tube (2).

15. A device according to claim 1, wherein the bending (11) closer than the bending (10) to the free end is 0.1 mm to 0.5 mm before the free end.

16. A device according to claim 1, wherein the device is configured for use at least one of in vitrectomies or for retinal peeling.

17. A device according to claim 1, wherein:

the different directions in which each of the two bendings (10, 11) is oriented are opposing directions; and the inner wall of the outer tube (1) and the outer wall of the inner tube (2) diverge relative to one another between the two bendings (10, 11).

18. A device according to claim 1, wherein the inner wall of the outer tube (1) and the outer wall of the inner tube (2) are not parallel relative to one another between the two bendings (10, 11).

* * * * *